(12) United States Patent
Gu

(10) Patent No.: US 11,494,368 B2
(45) Date of Patent: Nov. 8, 2022

(54) INFORMATION PROCESSING APPRATUS AND NON-TRANSITORY COMPUTER READABLE MEDIUM

(71) Applicant: FUJIFILM BUSINESS INNOVATION CORP., Tokyo (JP)

(72) Inventor: Jiali Gu, Kanagawa (JP)

(73) Assignee: FUJIFILM Business Innovation Corp., Tokyo (JP)

( * ) Notice: Subject to any disclaimer, the term of this patent is extended or adjusted under 35 U.S.C. 154(b) by 0 days.

(21) Appl. No.: 17/021,294

(22) Filed: Sep. 15, 2020

(65) Prior Publication Data
US 2021/0224248 A1 Jul. 22, 2021

(30) Foreign Application Priority Data

Jan. 22, 2020 (JP) .............................. JP2020-008751

(51) Int. Cl.
*G06F 16/23* (2019.01)
*G16H 10/60* (2018.01)
*G06F 3/0486* (2013.01)
(52) U.S. Cl.
CPC ........ *G06F 16/2365* (2019.01); *G06F 3/0486* (2013.01); *G16H 10/60* (2018.01)

(58) Field of Classification Search
CPC .... G06F 16/2365; G06F 3/0486; G16H 10/60
See application file for complete search history.

(56) References Cited

U.S. PATENT DOCUMENTS

| 7,933,048 B2 | 4/2011 | Koike |
| 2014/0279716 A1* | 9/2014 | Cormack ............... G06N 20/00 706/11 |
| 2017/0140251 A1* | 5/2017 | Nakagawa ........... G06K 9/6267 |
| 2017/0235436 A1* | 8/2017 | Hooton .................... H04L 67/10 705/7.11 |
| 2020/0118082 A1* | 4/2020 | Mehta ............... G06F 16/24573 |

FOREIGN PATENT DOCUMENTS

| JP | 4724428 B2 | 7/2011 |
| JP | 2015-32907 A | 2/2015 |
| JP | 5889628 B2 | 3/2016 |

* cited by examiner

*Primary Examiner* — Pei Yong Weng
(74) *Attorney, Agent, or Firm* — Oliff PLC

(57) ABSTRACT

An information processing apparatus includes a processor configured to cause a first region in which a sorted set, which is any of sets into which plural kinds of data have been sorted according to kind, is displayed and a second region in which data that is unsuitable for the sorted set is displayed to be displayed on an identical screen, receive selection of data displayed in the second region, and sort the received data into the sorted set displayed in the first region.

14 Claims, 14 Drawing Sheets

FIG. 10

| FORM-UNDER-CONFIRMATION ID | ORIGINAL DOCUMENT ID | DIGITALIZATION TIME AND DATE | DIGITALIZING DEVICE ID | PAGE CONFIGURATION |
|---|---|---|---|---|
| SN30037-1 | SN30037 | DECEMBER 30, 2019  10:00:30 | DEV5575 | 1, 3 |
| SN30037-2 | SN30037 | DECEMBER 30, 2019  10:00:30 | DEV5575 | 4, 5, 6, 7 |
| SN30037-6 | SN30037 | DECEMBER 30, 2019  10:00:30 | DEV5575 | 23, 24, 25, 26 |
| SN94911-3 | SN94911 | JANUARY 3, 2020  17:30:30 | DEV3373 | 10, 11, 12, 13 |

FIG. 11

| STRAY PAGE ID | ORIGINAL DOCUMENT ID | DIGITALIZATION TIME AND DATE | DIGITALIZING DEVICE ID | PAGE NUMBER |
|---|---|---|---|---|
| LOST-SN30037-2 | SN30037 | DECEMBER 30, 2019  10:00:30 | DEV5575 | 2 |
| LOST-SN30037-8 | SN30037 | DECEMBER 30, 2019  10:00:30 | DEV5575 | 8 |
| LOST-SN30037-9 | SN30037 | DECEMBER 30, 2019  10:00:30 | DEV5575 | 9 |
| LOST-SN30037-21 | SN30037 | DECEMBER 30, 2019  10:00:30 | DEV5575 | 21 |
| LOST-SN30037-22 | SN30037 | DECEMBER 30, 2019  10:00:30 | DEV5575 | 22 |
| LOST-SN94911-9 | SN94911 | JANUARY 3, 2020  17:30:30 | DEV3373 | 9 |
| LOST-SN94911-15 | SN94911 | JANUARY 3, 2020  17:30:30 | DEV3373 | 15 |

FIG. 12

| SUSPENDED FORM ID | ORIGINAL DOCUMENT ID | DIGITALIZATION TIME AND DATE | DIGITALIZING DEVICE ID | PAGE CONFIGURATION |
|---|---|---|---|---|
| HOLD-SN30037-3 | SN30037 | DECEMBER 30, 2019  10:00:30 | DEV5575 | 10, 11, 12, 13 |
| HOLD-SN30037-5 | SN30037 | DECEMBER 30, 2019  10:00:30 | DEV5575 | 19, 20 |
| HOLD-SN94911-1 | SN94911 | JANUARY 3, 2020  17:30:30 | DEV3373 | 1, 2 |

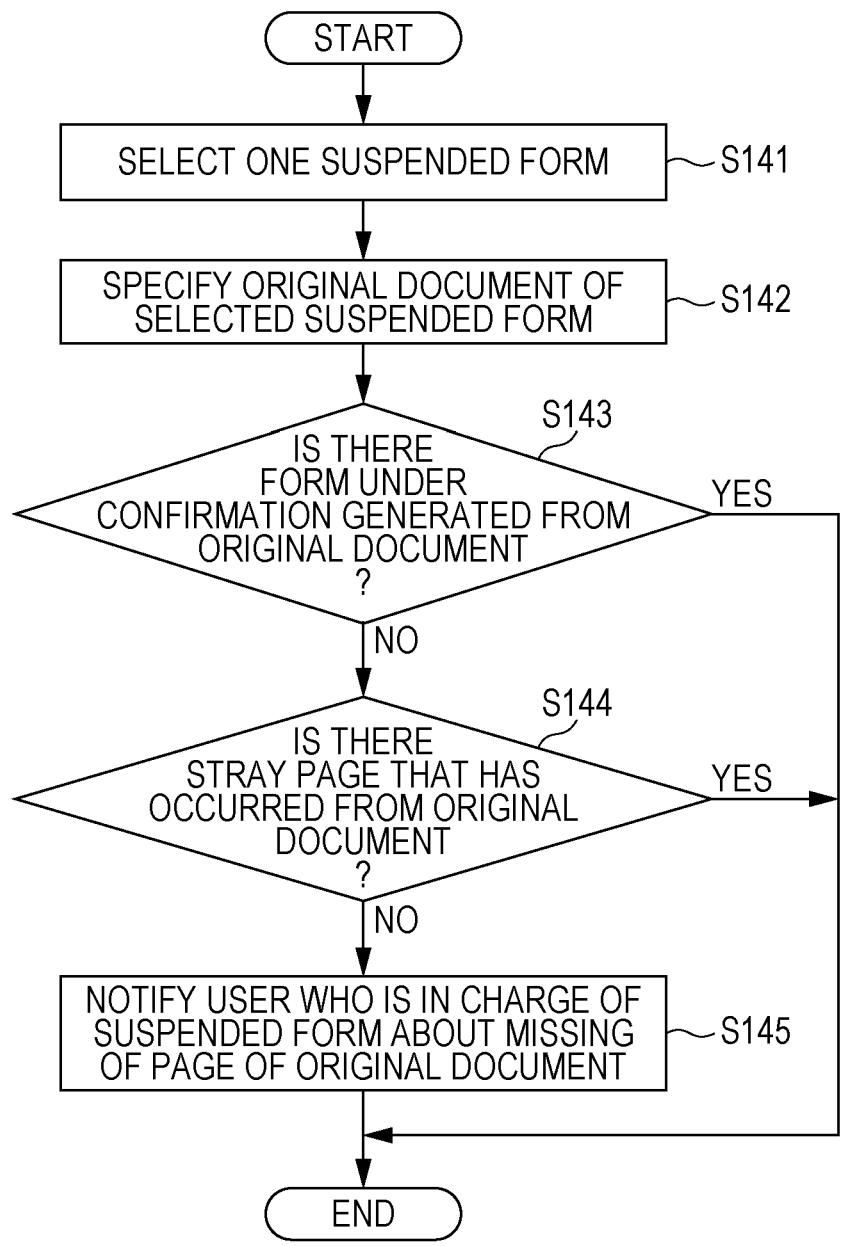

INFORMATION PROCESSING APPRATUS AND NON-TRANSITORY COMPUTER READABLE MEDIUM

CROSS-REFERENCE TO RELATED APPLICATIONS

This application is based on and claims priority under 35 USC 119 from Japanese Patent Application No. 2020-008751 filed Jan. 22, 2020.

BACKGROUND

(i) Technical Field

The present disclosure relates to an information processing apparatus and a non-transitory computer readable medium.

(ii) Related Art

An information processing apparatus is known that activates a collective display screen when a collective display button is pressed on a search list screen and causes image data sorted according to their type displayed on the search list screen to be successively displayed in an image data confirmation display region of the collective display screen per unit of the sorting (see, for example, Japanese Unexamined Patent Application Publication No. 2015-32907).

An image reading device is also known in which a controller generates form data of form document images assembled based on a designated type of form document on the basis of page information stored in an HD from form document images collectively scanned by a scanner and the generated form data is transmitted to a server device over a network (see, for example, Japanese Patent No. 4724428).

A medical electronic filing system is also known that includes a medical document issuing device that issues a medical document given a QR code (Registered Trademark), a printer that prints a medical document given a QR code, a scanner that scans a medical document to obtain a medical document image, a QR code analyzing device that arranges medical document images in a page order from page 1 to a last page for each document type code, a medical electronic filing device that sorts medical document images into medical electronic files and stores and registers the medical electronic files, and a medical document database (see, for example, Japanese Patent No. 5889628).

SUMMARY

In some cases, plural kinds of data are sorted into sets according to kind, and the sorted sets are managed. However, there may be data that is unsuitable for the sorted sets. That is, the data is not properly sorted in some cases. In such cases, a user needs to specify the unsuitable data from the sorted sets and put the unsuitable data into a correct set. Such a resorting operation is troublesome for the user.

Aspects of non-limiting embodiments of the present disclosure relate to a technique for sorting plural kinds of data into sets according to kind, in which user's trouble of resorting data is lessened as compared with a case where a result of sorted sets and data unsuitable for the sets are not displayed on an identical screen.

Aspects of certain non-limiting embodiments of the present disclosure overcome the above disadvantages and/or other disadvantages not described above. However, aspects of the non-limiting embodiments are not required to overcome the disadvantages described above, and aspects of the non-limiting embodiments of the present disclosure may not overcome any of the disadvantages described above.

According to an aspect of the present disclosure, there is provided an information processing apparatus including a processor configured to cause a first region in which a sorted set, which is any of sets into which plural kinds of data have been sorted according to kind, is displayed and a second region in which data that is unsuitable for the sorted set is displayed to be displayed on an identical screen, receive selection of data displayed in the second region, and sort the received data into the sorted set displayed in the first region.

BRIEF DESCRIPTION OF THE DRAWINGS

An exemplary embodiment of the present disclosure will be described in detail based on the following figures, wherein:

FIG. 10 illustrates an example of form-under-confirmation information stored in a form-under-confirmation information storage unit of the document processing apparatus according to the exemplary embodiment of the present disclosure;

FIG. 11 illustrates an example of stray page information stored in a stray page information storage unit of the document processing apparatus according to the exemplary embodiment of the present disclosure;

FIG. 12 illustrates an example of suspended form information stored in a suspended form information storage unit of the document processing apparatus according to the exemplary embodiment of the present disclosure;

FIG. 15 is a flowchart illustrating an example of operation of the notification processing unit of the document processing apparatus according to the exemplary embodiment of the present disclosure.

DETAILED DESCRIPTION

Figure 1:
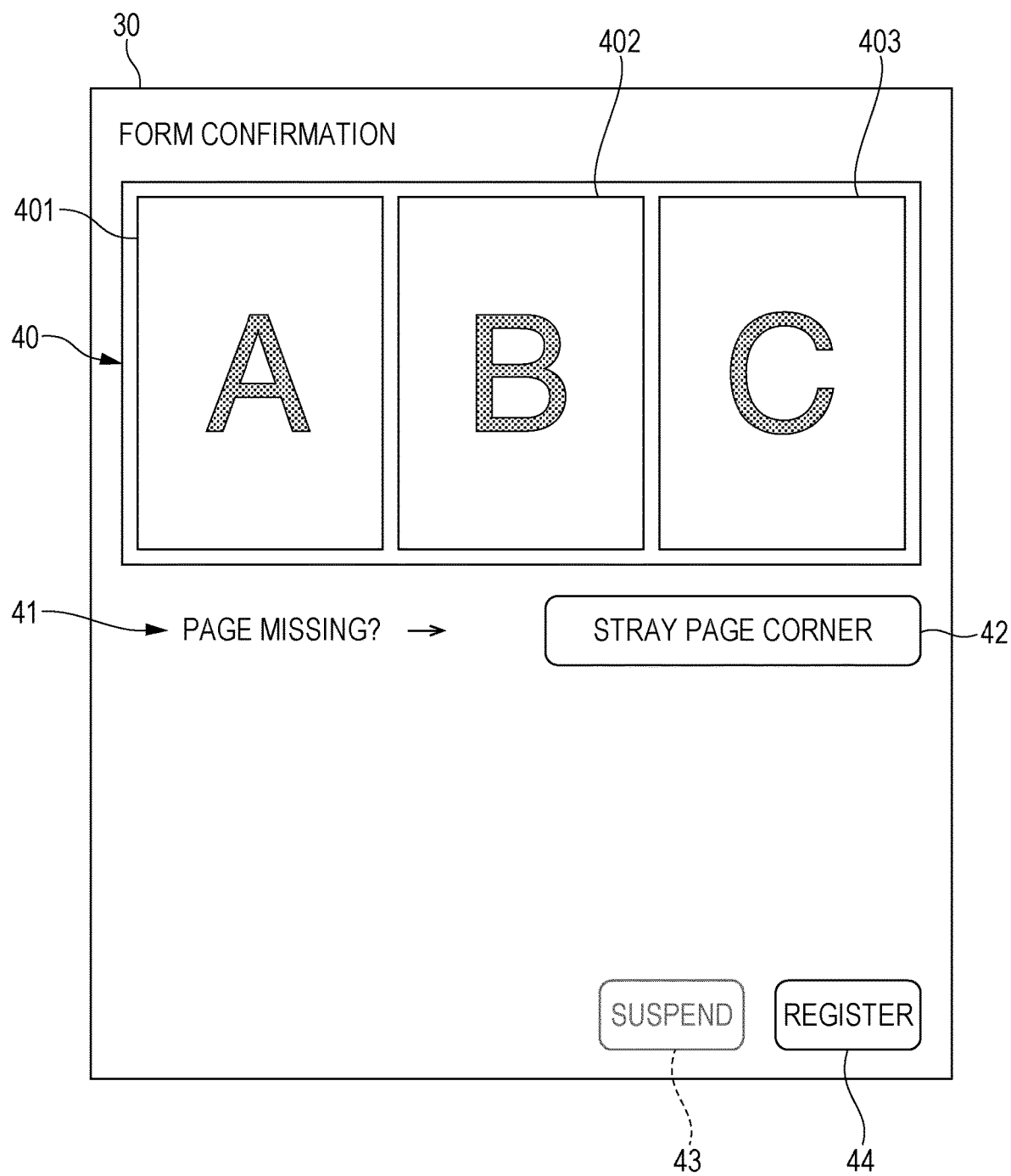
FIG. 1 illustrates an example of an initial state of a form confirmation screen displayed by a document processing apparatus according to an exemplary embodiment of the present disclosure.

An exemplary embodiment of the present disclosure is described in detail below with reference to the attached drawings.

Summary of Present Exemplary Embodiment

In the present exemplary embodiment, a document processing apparatus 10 displays, on an identical screen, a first region where sets into which plural kinds of data have been sorted according to kind are displayed and a second region where data unsuitable for the sorted sets is displayed. In the first region, information (e.g., thumbnails of data included in the sets) by which the sorted sets can be identified need just be displayed.

Furthermore, the document processing apparatus 10 may receive user's selection of data unsuitable for the sets displayed in the first region and move the received data to the second region. Note that a sorting condition may be set in advance and data that does not meet this condition may be moved to the second region without user's selection of data. Furthermore, the document processing apparatus 10 may receive user's selection of data displayed in the second region and put the received data into a set displayed in the first region. Furthermore, in a case where a sorted set has a missing part, this set may be managed as a suspended set. The suspended set is a set whose sorting has not been properly completed due to a missing part.

Although the data may be a general electronic document, the following discusses an example in which the data is an electronic document of a form obtained by reading a form document by an image reading device. The set is a collection of data classified according to kind of documents, and the following discusses an example in which the set is a group of electronic document pages (hereinafter referred to as a "sorted form") of forms sorted according to kind. Furthermore, a unit of data may be any unit of data that constitutes a sorted form, and the following discusses an example in which the unit of data is a page that constitutes a sorted form.

The following discusses an example in which the first region is a form confirmation region of a form confirmation screen and the second region is a stray page corner of the form confirmation screen. In the present exemplary embodiment, operability of moving a page from the form confirmation region to the stray page corner and moving a page from the stray page corner to the form confirmation region is improved since the form confirmation region and the stray page corner are displayed on an identical screen. Furthermore, the following discusses an example in which management as a suspended set (referred to as a "suspended form" in the following examples) is management of a sorted form in a suspended form corner.

First, a form confirmation screen 30 displayed by the document processing apparatus 10 is described. The form confirmation screen 30 is a screen for confirming contents of a sorted form after sorting of electronic documents of forms. A user can move from and to the form confirmation screen 30 to and from a stray page corner 50 and a suspended form corner 70, which will be described later.

FIG. 1 illustrates an example of an initial state of the form confirmation screen 30.

As illustrated in FIG. 1, the form confirmation screen 30 includes a form confirmation region 40, a guide message 41, a stray page corner button 42, a suspension button 43, and a registration button 44.

The form confirmation region 40 is a region for checking whether or not a sorted form includes a page (hereinafter referred to as a "misplaced page") that is irrelevant with the sorted form and whether or not a page (hereinafter referred to as a "missing page") that should be included in a sorted form is missing from the sorted form. In FIG. 1, thumbnail images 410 to 403 of pages of a sorted form (hereinafter referred to as a "form under confirmation") that is being confirmed are disposed within the form confirmation region 40.

The guide message 41 is a message for guiding a user to press a stray page corner button 42 in a case where a page is missing from the sorted form.

The stray page corner button 42 is a button for unfolding the stray page corner 50. When a user notices that a page is missing from the form under confirmation in the form confirmation region 40 and presses the stray page corner button 42, the stray page corner 50 is unfolded. The stray page corner 50 is a mechanism that holds and manages, as a stray page, a misplaced page discovered after sorting of electronic documents of forms. In a case where the user finds the missing page by referring to stray pages that are managed in the stray page corner 50, the user adds the missing page to the form under confirmation.

The suspension button 43 is a button for putting the form under confirmation into the suspended form corner 70. In a case where the user cannot find the missing page in the unfolded stray page corner 50, the user suspends the processing and presses the suspension button 43. This causes the form under confirmation to be put into the suspended form corner 70. The suspended form corner 70 is a mechanism that holds and manages, as a suspended form, a form under confirmation for which a user has found that a page is missing after sorting of electronic documents of forms and has determined that the missing page cannot be filled by a stray page.

The registration button 44 is a button for registering a form under confirmation without a misplaced page or a missing page as a correct sorted form. When the user presses the registration button 44 in a case where there is no misplaced page or missing page in the form under confirmation in the form confirmation region 40, in a case where a misplaced page found in the form under confirmation in the form confirmation region 40 has been put into the stray page corner 50 as described later, or in a case where a page found to be missing from the form under confirmation in the form confirmation region 40 has been filled by a stray page of the stray page corner 50 as described above, the form under confirmation is registered as a correct sorted form.

Figure 2:
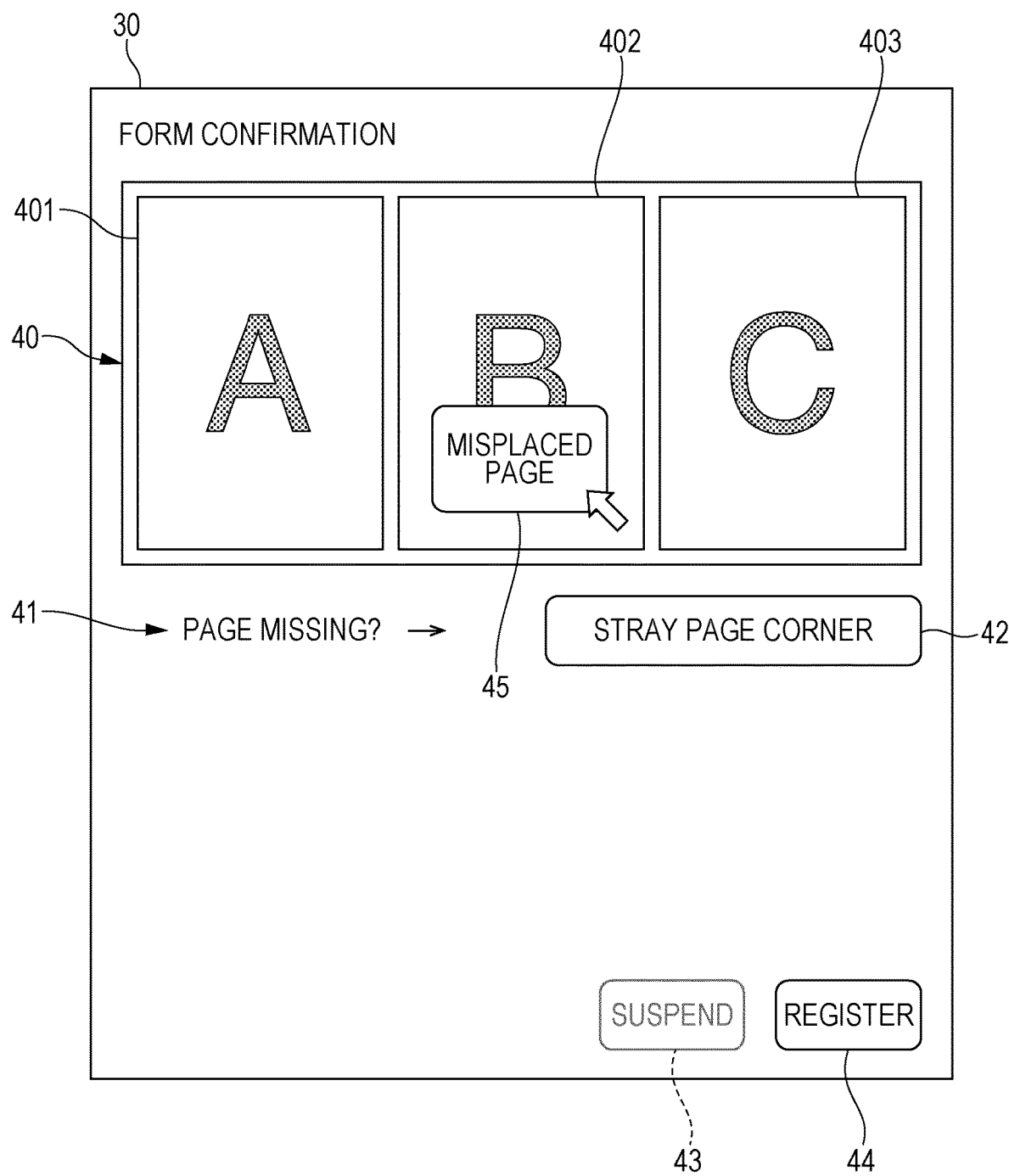
FIG. 2 illustrates an example of transition of a state of the form confirmation screen that occurs when a misplaced page of a form under confirmation is put into a stray page corner.
Figure 3:
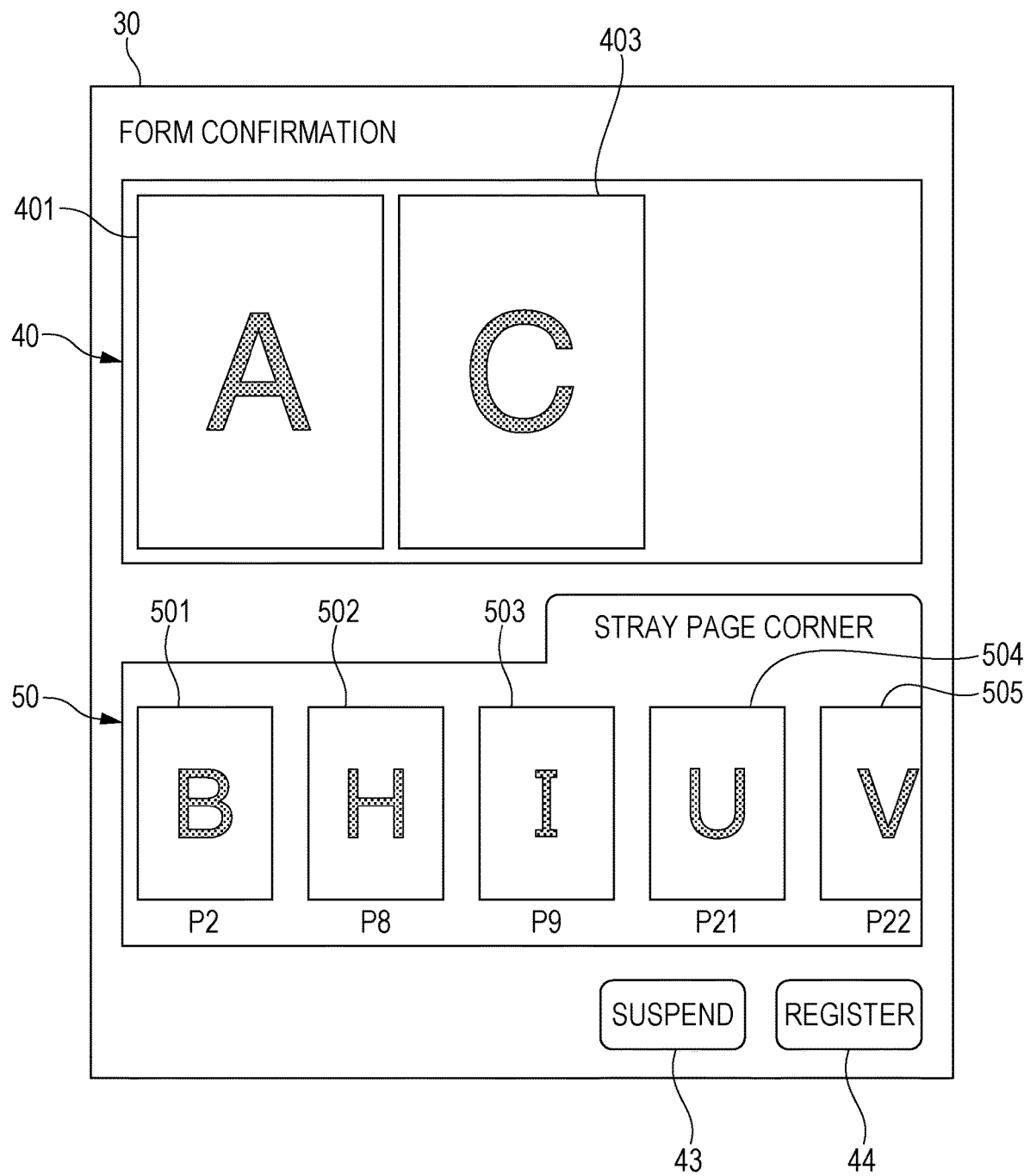
FIG. 3 illustrates an example of transition of a state of the form confirmation screen that occurs when a misplaced page of a form under confirmation is put into a stray page corner.

FIGS. 2 and 3 illustrate an example of transition of a state of the form confirmation screen 30 that occurs when a misplaced page of the form under confirmation is put into the stray page corner 50.

FIG. 2 illustrates an example of a state of the form confirmation screen 30 displayed when a user finds a misplaced page in the form under confirmation and gives an instruction to put the misplaced page into the stray page corner 50.

In FIG. 2, when the user places a mouse cursor on a thumbnail image of any page of the form under confirmation, a misplaced page button 45 appears. Accordingly, the user places a mouse cursor on the thumbnail image 402 of the misplaced page so that the misplaced page button 45 is displayed on the thumbnail image 402. When the user clicks the misplaced page button 45 in this state, the misplaced page is deleted from the form under confirmation and is moved to the stray page corner 50. That is, when the user selects a page of the form under confirmation, a button for moving the selected page to the stray page corner 50 is displayed, and one action (e.g., one click) on the button can move the selected page to the stay page corner 50. Note that a confirmation screen asking for permission to move the misplaced page may be displayed before the misplaced page is moved to the stray page corner 50.

FIG. 3 illustrates an example of a state of the form confirmation screen 30 displayed when the stray page corner 50 is unfolded after the misplaced page is put into the stray page corner 50.

FIG. 3 illustrates a state where thumbnail images 501 to 505 of stray pages are disposed within the stray page corner 50. In a case where the stray page corner 50 is unfolded while the form under confirmation is being displayed in the form confirmation region 40, the thumbnail images 501 to 505 of the stray pages may be displayed in a descending order of similarity with the form under confirmation in the stray page corner 50.

The misplaced page is an example of data that is unsuitable for a set displayed in the first region. Examples of this unsuitable data include data that has been visually determined as being unsuitable and given some sort of instruction by a user and data that has been determined as unknown data that cannot be classified into any kind according to some sort of condition or database by a computer.

Figure 4:
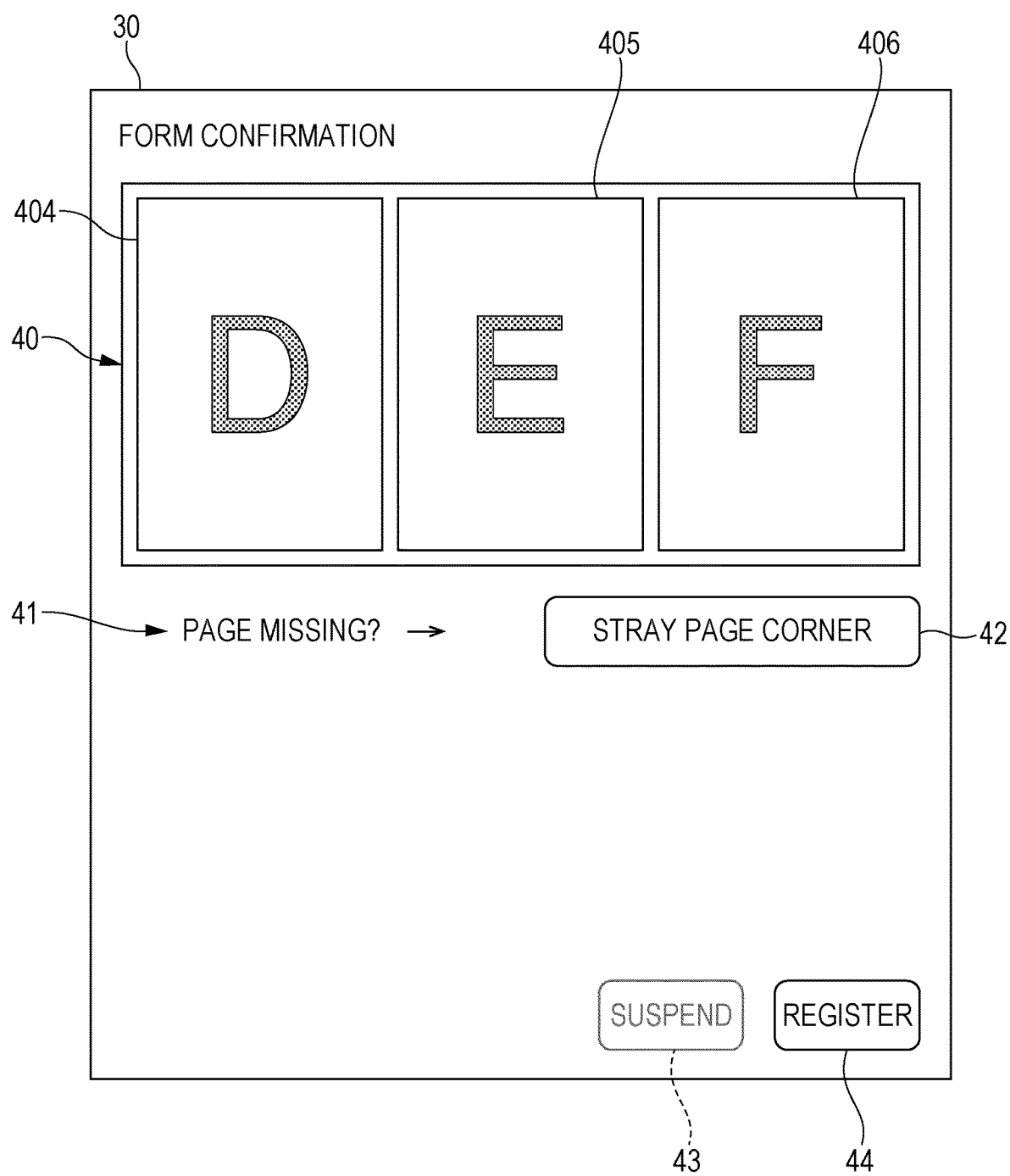
FIG. 4 illustrates an example of transition of a state of the form confirmation screen that occurs when a missing page of a form under confirmation is filled by a page in the stray page corner.
Figure 5:
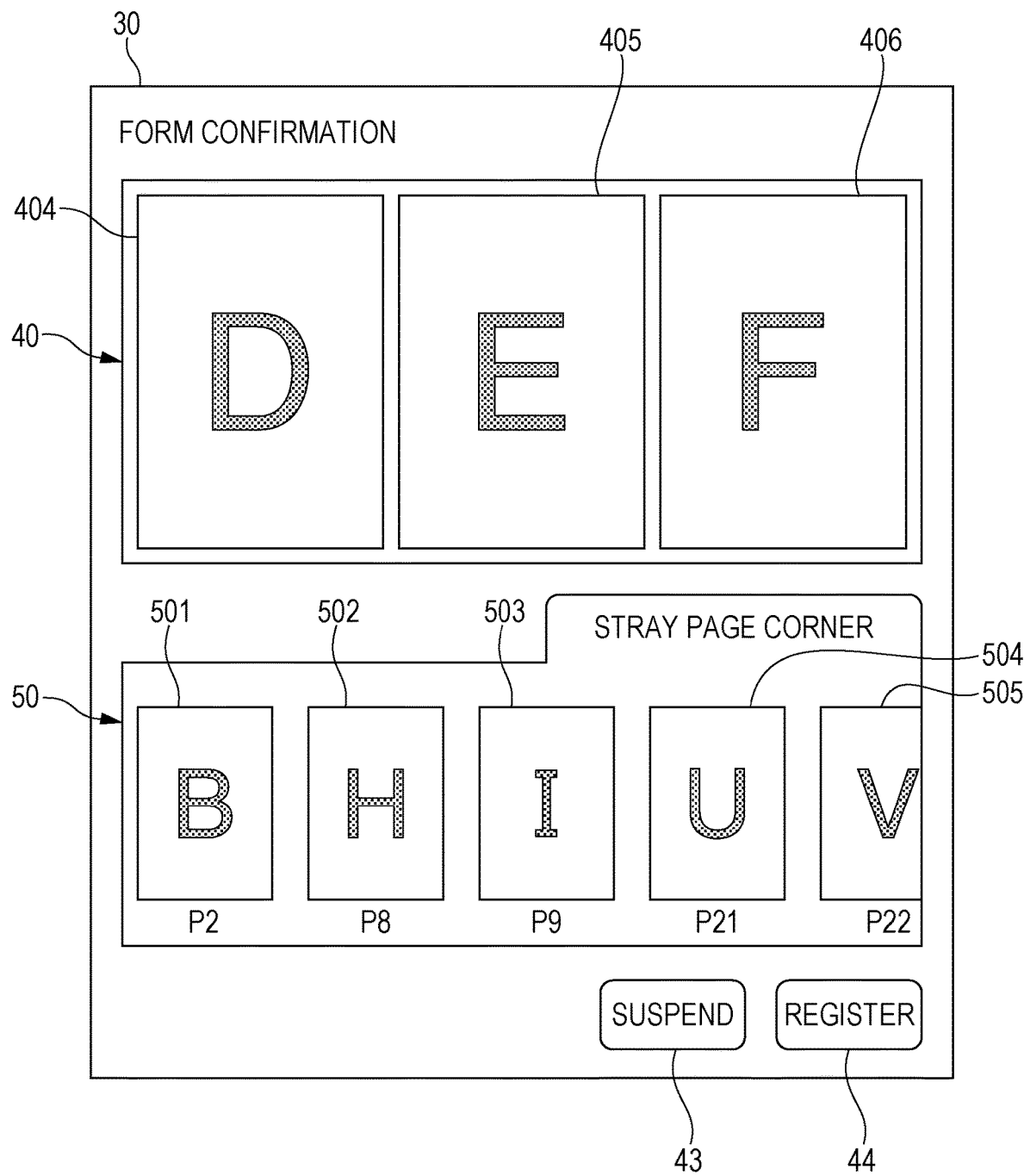
FIG. 5 illustrates an example of transition of a state of the form confirmation screen that occurs when a missing page of a form under confirmation is filled by a page in the stray page corner.
Figure 6:
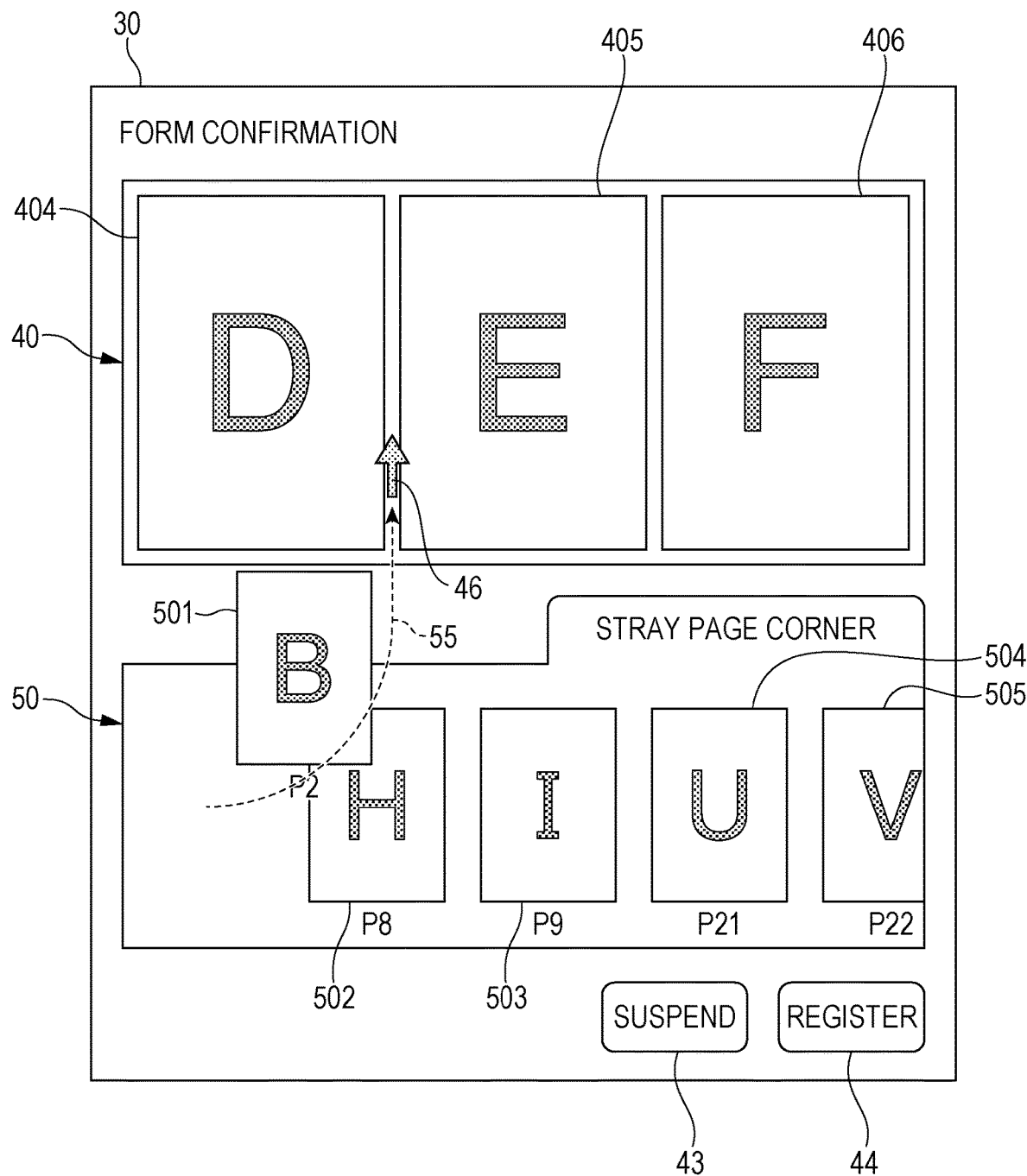
FIG. 6 illustrates an example of transition of a state of the form confirmation screen that occurs when a missing page of a form under confirmation is filled by a page in the stray page corner.

FIGS. 4 through 6 illustrate an example of transition of a state of the form confirmation screen 30 that occurs when a missing page of a form under confirmation is filled by a page found from the stray page corner 50.

FIG. 4 illustrates an example of a state of the form confirmation screen 30 on which a form under confirmation different from the form under confirmation of FIG. 1 is displayed.

FIG. 4 illustrates a state where thumbnail images 404 to 406 of pages of the form under confirmation are disposed within the form confirmation region 40.

FIG. 5 illustrates an example of a state of the form confirmation screen 30 displayed when a user finds that a page is missing from the form under confirmation.

FIG. 5 illustrates a state where the thumbnail images 501 to 505 of the stray pages are disposed within the stray page corner 50 as in FIG. 3. It is assumed that the user finds that a page is missing from the form under confirmation disposed in the form confirmation region 40 in this state.

FIG. 6 illustrates an example of a state of the form confirmation screen 30 displayed when the user unfolds the stray page corner 50, finds the missing page from among the stray pages, and inserts the missing page into the form under confirmation.

In FIG. 6, the user finds the missing page in the stray page corner 50 and inserts the missing page into the form under confirmation by dragging and dropping the thumbnail image 501 of this missing page as indicated by a broken arrow 55. In this process, an arrow object 46 indicating a place into which the missing page is to be inserted may be displayed in the form confirmation region 40. In this case, the place into which the missing page is to be inserted may be determined on the basis of a relationship between page numbers of the pages of the form under confirmation managed in form-under-confirmation information, which will be described later, and a page number of the stray page managed in stray page information, which will be described later.

Meanwhile, in a case where the missing page cannot be found in the stray page corner 50 in FIG. 5, the user suspends the operation of confirming the form under confirmation and presses the suspension button 43. This causes the form under confirmation to be sent to the suspended form corner 70.

The suspension button 43 is grayed out and cannot be pressed on the form confirmation screen 30 of FIG. 4, whereas the suspension button 43 is no longer grayed out and can be pressed on the form confirmation screen 30 of FIG. 5. This is because the user has confirmed the stray pages in the stray page corner 50 on the form confirmation screen 30 of FIG. 5. The user is thus prevented from pressing the suspension button 43 and putting the form under confirmation into the suspended form corner 70 without confirming the stray pages. If the user puts the form under confirmation into the suspended form corner 70 without confirming the stray pages, a large number of suspended forms whose missing pages are in the stray page corner 50 are put into the suspended form corner 70. Therefore, it becomes hard to find out a missing page from the stray page corner 50 later. During confirmation of an initial form, no stray page is present in the stray page corner 50, and therefore the suspension button 43 is not grayed out and can be pressed even in a case where the stray page corner 50 has not been unfolded or even in a case where no stray page is displayed although the stray page corner 50 has been unfolded. In the present exemplary embodiment, a condition that the stray page corner 50 has not been unfolded or no stray page is displayed although the stray page corner 50 has been unfolded is used as an example of a condition that no data is displayed in the second region, and a condition that the user has confirmed stray pages is used as an example of a condition that the user has confirmed all data displayed in the second region. Whether or not the user has confirmed the stray page may be determined based on whether or not the user has made some sort of action on the stray page corner 50. Examples of such an action include an action of unfolding the stray page corner 50, an action of scrolling the stray page corner 50 to the last, and an action of pressing a confirmation button (not illustrated) provided in the stray page corner 50.

Note that a condition for shifting to the state where the suspension button 43 is no longer grayed out and can be pressed can be any condition related to the stray page corner 50. In the present exemplary embodiment, a condition related to the stray page corner 50 is used as an example of a specific condition related to the second region. Furthermore, permitting the form under confirmation to be put into the suspended form corner 70 in a case where the condition related to the stray page corner 50 is met is used as an example of managing a sorted set as a suspended set in a case where a specific condition is met, and prohibiting the form under confirmation from being put into the suspended form corner 70 in a case where the condition related to the stray page corner 50 is not met is used as an example of not managing a sorted set as a suspended set in a case where the specific condition is not met.

In a case where there is no longer a misplaced page nor a missing page in the form under confirmation in FIG. 3 or FIG. 6, the user presses the registration button 44. This causes the form under confirmation to be registered as a correct sorted form.

Next, a suspended form screen 60 displayed by the document processing apparatus 10 is described.

Figure 7:
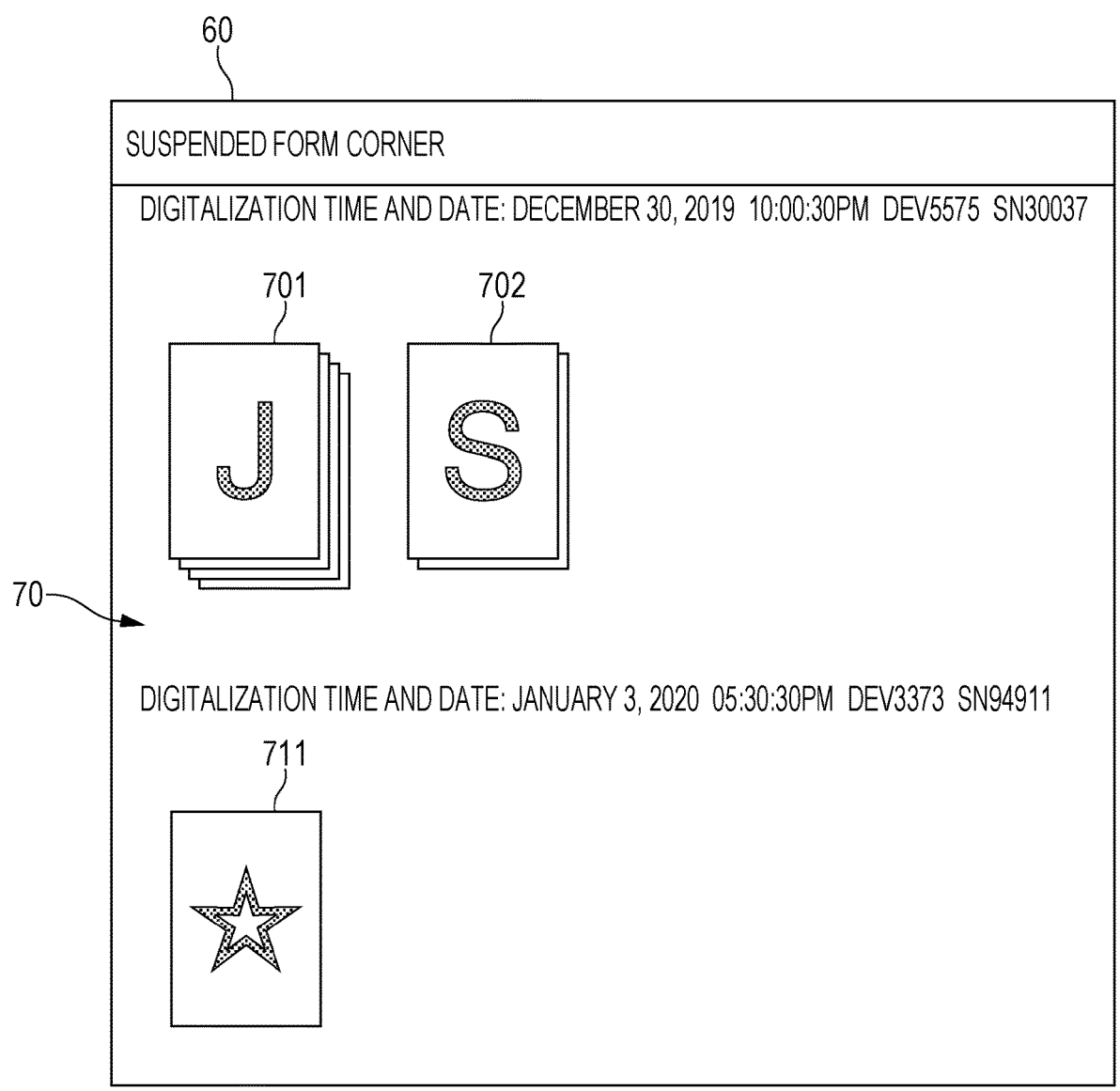
FIG. 7 illustrates an example of a suspended form screen displayed by the document processing apparatus according to the exemplary embodiment of the present disclosure.

FIG. 7 illustrates an example of the suspended form screen 60.

As illustrated in FIG. 7, the suspended form screen 60 includes the suspended form corner 70. FIG. 7 illustrates a state where thumbnail images 701, 702, and 711 of suspended forms are disposed within the suspended form corner 70. The user opens the confirmation screen again to resume confirmation of the suspended form within the suspended form corner 70. In the suspended form corner 70, the suspended form may be grouped on the basis of digitalization time and date, a digitalizing device ID, and a unique form ID given at the time of digitalization as illustrated in FIG. 7.

Hardware Configuration of Document Processing Apparatus

Figure 8:
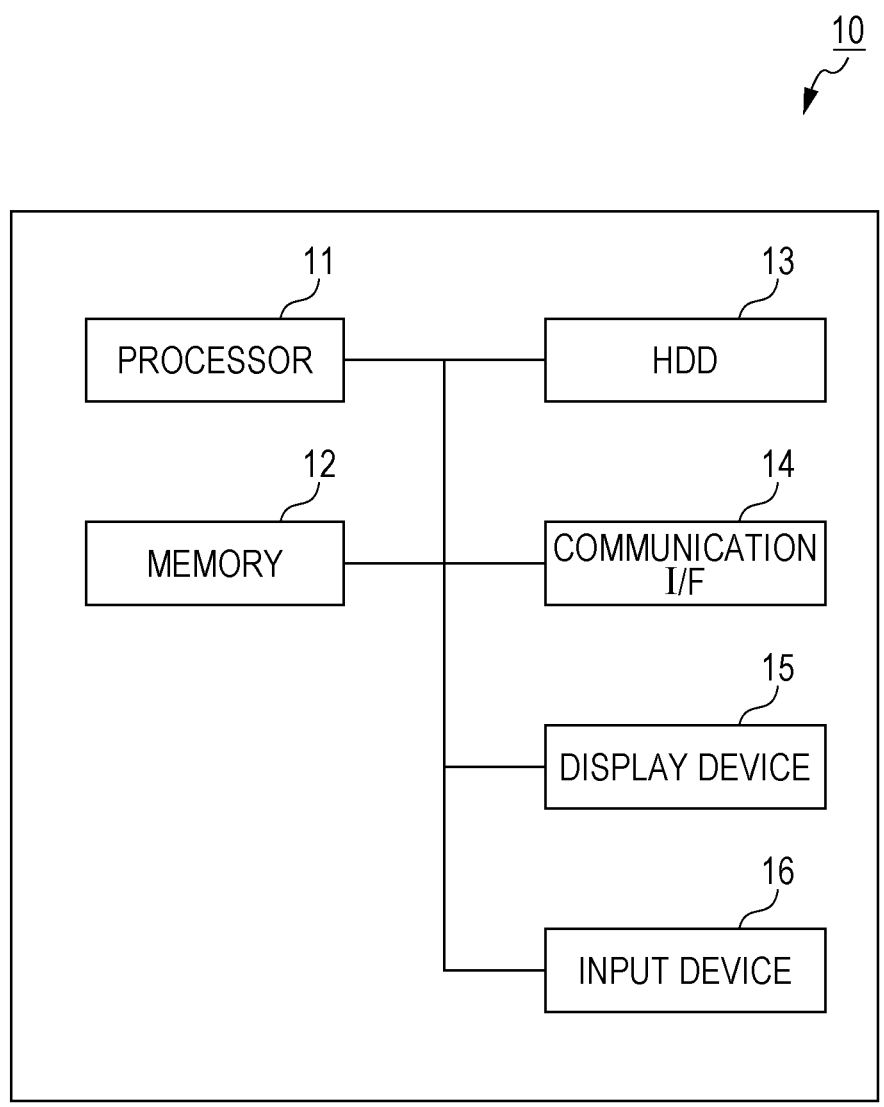
FIG. 8 illustrates an example of a hardware configuration of the document processing apparatus according to the exemplary embodiment of the present disclosure.

FIG. 8 illustrates an example of a hardware configuration of the document processing apparatus 10 according to the present exemplary embodiment. As illustrated in FIG. 8, the document processing apparatus 10 includes a processor 11, which is a computing unit, a memory 12, which is a storage unit, and a hard disk drive (HDD) 13. The processor 11 executes various kinds of software such as an operating system (OS) and an application and thus realizes various functions, which will be described later. The memory 12 is a storage region in which various kinds of software, data used for execution of the software, and the like are stored, and the HDD 13 is a storage region in which data input to the various kinds of software, data output from the various kinds of software, and the like are stored. Furthermore, the document processing apparatus 10 includes a communication I/F 14 for communication with an outside, a display device 15 such as a display, and an input device 16 such as a keyboard or a mouse.

Functional Configuration of Document Processing Apparatus

Figure 9:
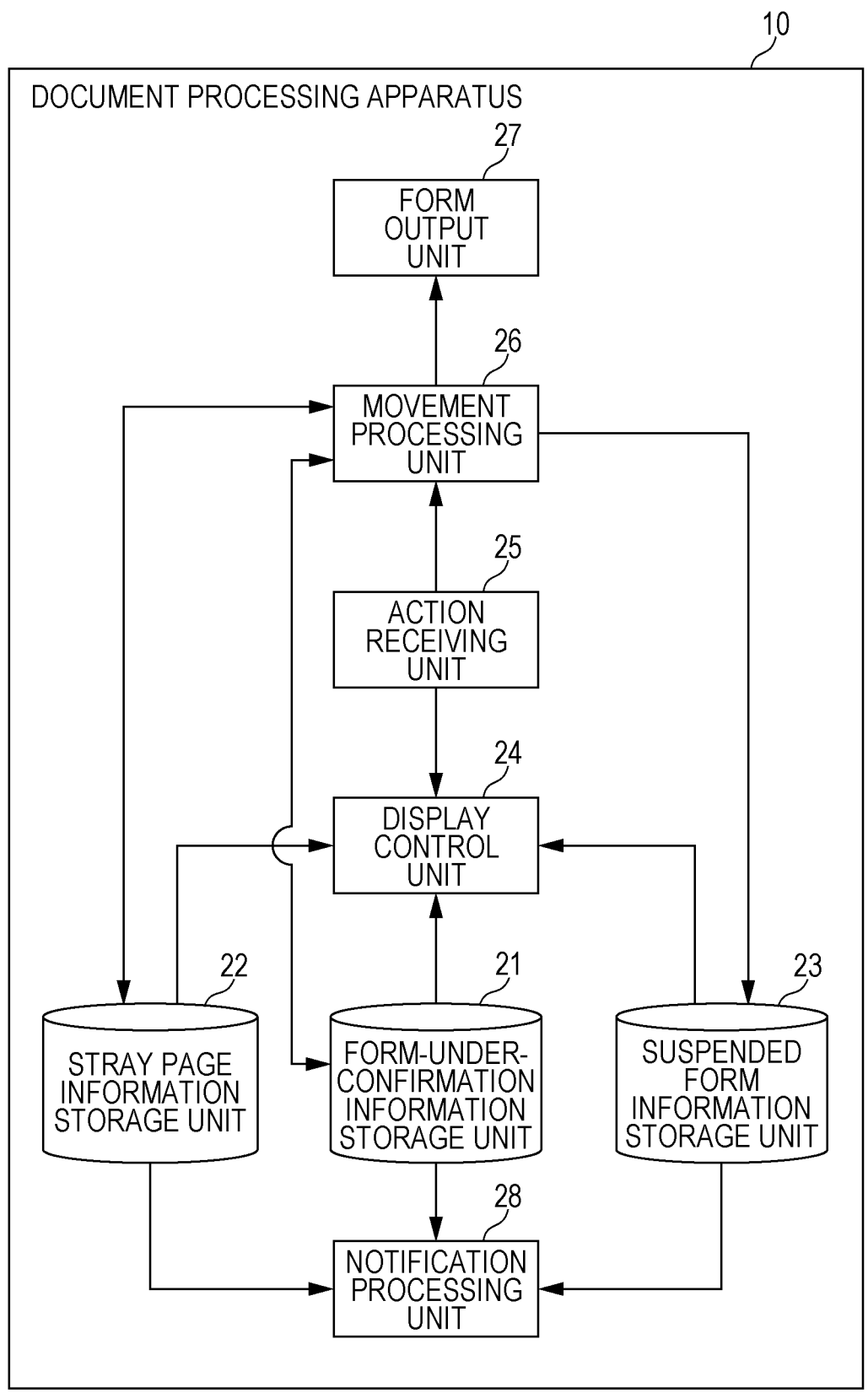
FIG. 9 is a block diagram illustrating an example of a functional configuration of the document processing apparatus according to the exemplary embodiment of the present disclosure.

FIG. 9 is a block diagram illustrating an example of a functional configuration of the document processing apparatus 10 according to the present exemplary embodiment. The document processing apparatus 10 according to the present exemplary embodiment is an example of an information processing apparatus and includes a form-under-confirmation information storage unit 21, a stray page information storage unit 22, a suspended form information storage unit 23, a display control unit 24, an action receiving unit 25, a movement processing unit 26, a form output unit 27, and a notification processing unit 28, as illustrated in FIG. 9.

The form-under-confirmation information storage unit 21 stores therein information (hereinafter referred to as "form-under-confirmation information") on a form under confirmation disposed in the form confirmation region 40. A specific example of the form-under-confirmation information will be described later.

The stray page information storage unit 22 stores therein information (hereinafter referred to as "stray page information") on a stray page disposed in the stray page corner 50. A specific example of the stray page information will be described later.

The suspended form information storage unit 23 stores therein information (hereinafter referred to as "suspended form information") on a suspended form disposed in the suspended form corner 70. A specific example of the suspended form information will be described later.

The display control unit 24 controls the display device 15 to display thumbnail images of pages of a form under confirmation in the form confirmation region 40 on the basis of the form-under-confirmation information stored in the form-under-confirmation information storage unit 21.

When the action receiving unit 25 receives an action of pressing the stray page corner button 42, the display control unit 24 controls the display device 15 to unfold and display the stray page corner 50 on the screen on which the form confirmation region 40 is displayed. Then, the display control unit 24 controls the display device 15 to display a stray page in the stray page corner 50 on the basis of the stray page information stored in the stray page information storage unit 22. In the present exemplary embodiment, the display control unit 24 is an example of a unit that causes the first region and the second region to be displayed on an identical screen.

In this process, the display control unit 24 may desirably cause a stray page including information similar to information on the form under confirmation displayed in the form confirmation region 40 to be preferentially displayed in the stray page corner 50. This is an example of preferentially displaying, in the second region, data including information similar to information on a set displayed in the first region. One example of the stray page including information similar to information on the form under confirmation displayed in the form confirmation region 40 is a stray page that is close in page order to the pages of the form under confirmation among stray pages read by the same image reading device as the form under confirmation at the same time and date as the form under confirmation. Another example is a stray page read by an image reading device within a predetermined range from an image reading device used to read the form under confirmation at time and date within a predetermined range from time and date of the reading of the form under confirmation. This is an example of data read by an image reading device within a predetermined range from an image reading device used to read a set displayed in the first region at time and date within a predetermined range from time and date of the reading of the set displayed in the first region. This is because in a case where a single document is divided into plural parts and the plural parts are scanned by plural users, it is highly likely that the plural parts are read by image reading devices that are within a close range at close times and dates even if the plural parts are not read by the same image reading device at the same time and date. The image reading devices within a predetermined range are, for example, image reading devices that are physically close to one another or image reading devices that are provided in an identical department or close departments. Another example of the stray page including information similar to information on the form under confirmation displayed in the form confirmation region 40 is a stray page having a layout similar to layouts of the pages of the form under confirmation.

The wording "preferentially" refers to displaying a stray page including information similar to information on the form under confirmation displayed in the form confirmation region 40 in a manner such that this stray page is easier to select. For example, in a case where not all stray pages can be displayed in the stray page corner 50, displaying, in the stray page corner 50, the stray page including information similar to information on the form under confirmation displayed in the form confirmation region 40 is "preferentially" displaying the stray page, and not displaying, in the stray page corner 50, the stray page including information similar to information on the form under confirmation displayed in the form confirmation region 40 is not "preferentially" displaying the stray page. Alternatively, in a case where all stray pages can be displayed by scrolling the stray page corner 50, displaying, in a part that can be viewed without scrolling the stray page corner 50, the stray page including information similar to information on the form under confirmation displayed in the form confirmation region 40 is "preferentially" displaying the stray page, and displaying, in a part that cannot be viewed without scrolling the stray page corner 50, the stray page including information similar to information on the form under confirmation displayed in the form confirmation region 40 is not "preferentially" displaying the stray page.

Furthermore, the display control unit 24 controls the display device 15 to display a suspended form in the suspended form corner 70 of the suspended form screen 60 on the basis of the suspended form information stored in the suspended form information storage unit 23.

The action receiving unit 25 receives a user's action on the form confirmation screen 30 and the suspended form screen 60. For example, on the form confirmation screen 30, the action receiving unit 25 receives actions such as an action of pressing the stray page corner button 42, the suspension button 43, the registration button 44, or the misplaced page button 45 and an action of dragging and dropping a stray page disposed in the stray page corner 50 into the form confirmation region 40. In the present exemplary embodiment, the action receiving unit 25 is an example of a unit that receives selection of data that is unsuitable for the set displayed in the first region or a unit that receives selection of data that is displayed in the second region.

When the action receiving unit 25 receives an operation of pressing the misplaced page button 45 on a misplaced page of the form under confirmation disposed in the form confirmation region 40, the movement processing unit 26 moves this misplaced page from the form confirmation region 40 to the stray page corner 50. Specifically, the movement processing unit 26 deletes a part concerning this misplaced page in form-under-confirmation information concerning this form under confirmation from the form-under-confirmation information storage unit 21 and adds this part as stray page information on this misplaced page to the stray page information storage unit 22. In this case, the movement processing unit 26 is an example of a unit that moves the received data to the second region.

Furthermore, when the action receiving unit 25 receives an action of dragging and dropping a stray page disposed in the stray page corner 50 onto a part between pages of the form under confirmation disposed in the form confirmation region 40, the movement processing unit 26 moves this stray page from the stray page corner 50 to the form confirmation region 40. Specifically, the movement processing unit 26 deletes stray page information concerning this stray page from the stray page information storage unit 22 and stores this stray page information as a part concerning this stray page in the form-under-confirmation information on the form under confirmation into which the stray page has been inserted in the form-under-confirmation information storage unit 21. In this case, the movement processing unit 26 is an example of a unit that sorts the received data into a set displayed in the first region.

Furthermore, when the action receiving unit 25 receives an action of pressing the suspension button 43 on the form confirmation region 40, the movement processing unit 26 moves the form under confirmation displayed in the form confirmation region 40 to the suspended form corner 70. Specifically, the movement processing unit 26 deletes form-under-confirmation information concerning this form under confirmation from the form-under-confirmation information storage unit 21 and stores this form-under-confirmation information as suspended form information concerning this form under confirmation in the suspended form information storage unit 23.

Furthermore, when the action receiving unit 25 receives an action of pressing the registration button 44 on the form confirmation region 40, the movement processing unit 26 delivers the form under confirmation displayed in the form confirmation region 40 to the form output unit 27 to register this form under confirmation as a correct sorted form. Specifically, the movement processing unit 26 deletes form-under-confirmation information concerning this form under confirmation from the form-under-confirmation information storage unit 21.

The form output unit 27 outputs, to an outside, the form under confirmation delivered by the movement processing unit 26 when the action receiving unit 25 receives the action of pressing the registration button 44. The outside may be any system or device that performs processing next to the processing in the document processing apparatus 10.

The notification processing unit 28 regularly monitors states of the stray page corner 50 and the suspended form corner 70 and gives the following notification.

First, in a case where a new stray page arrives at the stray page corner 50, the notification processing unit 28 gives a notification to persons in charge of suspended forms within the suspended form corner 70. This notification is a notification inquiring whether or not the stray page that has newly arrived at the stray page corner 50 is a page missing from the suspended forms which the persons are in charge of. This is an example of giving the user a notification indicating that new data has been added to the second region when the new data is added to the second region. Entry of information on a person in charge may be received before a form document is read or before an electronic document of a form is sorted, and the information may be associated with the electronic document of the form. Furthermore, the information may be taken over from the electronic document of the form and associated with a sorted form. Alternatively, entry of information on a person in charge may be received after sorting, and the information may be associated with a sorted form.

In this process, the notification processing unit 28 may desirably preferentially give the notification to a user who is in charge of a suspended form including information similar to information on the newly-arrived stray page. This is an example of preferentially giving a notification indicating that new data has been added to the second region to a user related to a set including information similar to information on the new data added to the second region. One example of the suspended form including information similar to information on the newly-arrived stray page is a suspended form read by the same image reading device as the newly-arrived stray page at the same time and date as the newly-arrived stray page. Another example is a suspended form read by an image reading device within a predetermined range from an image reading device used to read the newly-arrived stray page at time and date within a predetermined range from time and date of the reading of the newly-arrived stray page. This is an example of a set read by an image reading device within a predetermined range from an image reading device used to read the new data added to the second region at time and date within a predetermined range from time and date of the reading of the new data added to the second region. This is because, in a case where a single document is divided into plural parts and the plural pages are scanned by plural users, it is highly likely that the plural parts are read by image reading devices that are in a close range at close times and dates even if the plural parts are not read by the same image reading device at the same time and date. The image reading devices within a predetermined range are, for example, image reading devices that are physically close to one another or image reading devices that are provided in an identical department or close departments. Another example of the suspended form including information similar to information on the newly-arrived stray page is a suspended form having a layout similar to a layout of the stray page.

The wording "preferentially" means that the notification is given so that a user who is in charge of the suspended form including information similar to information on the newly-arrived stray page notices the notification early. For example, giving the notification to a user who is in charge of the suspended form including information similar to information on the newly-arrived stray page earlier than other users is "preferentially" giving the notification, and giving the notification to a user who is in charge of the suspended form including information similar to information on the newly-arrived stray page later than the other users is not "preferentially" giving the notification. Alternatively, more frequently giving the notification to a user who is in charge of the suspended form including information similar to information on the newly-arrived stray page than the other users is "preferentially" giving the notification, and less frequently giving the notification to a user who is in charge of the suspended form including information similar to information on the newly-arrived stray page than the other users is not "preferentially" giving the notification.

Furthermore, in a case where a new suspended form occurs in the suspended form corner 70, the notification processing unit 28 determines whether or not the new suspended form has occurred not because erroneous sorting has occurred but because a document page is missing from the start, and in a case where the new suspended form has occurred because a document page is missing from the start, gives a notification prompting a person in charge of the suspended form to deal with this. This is an example of, in a case where a missing part of a sorted set managed as a suspended set is unlikely to be filled, giving a notification indicating that the missing part of the suspended set is unlikely to be filled to a user who is related to the suspended set. The case where the missing part of the suspended set is unlikely to be filled is, for example, a case where a stray page that fills a missing page of the suspended form is not in the stray page corner 50.

FIG. 10 illustrates an example of form-under-confirmation information stored in the form-under-confirmation information storage unit 21.

As illustrated in FIG. 10, the form-under-confirmation information is information in which a form-under-confirmation ID, an original document ID, digitalization time and date, a digitalizing device ID, and a page configuration are associated with one another.

The form-under-confirmation ID is identification information for identifying a form under confirmation. Hereinafter, a form under confirmation given a form-under-confirmation ID "X" is referred to as a "form under confirmation X".

The original document ID is identification information for identifying a document from which a form under confirmation identified by a corresponding form-under-confirmation ID was generated. Since forms obtained by digitalizing a single original document at the same digitalization time and date by the same digitalizing device are sorted into plural forms under confirmation, forms under confirmation that are identical in digitalization time and date and digitalizing device ID are given the same original document ID. Hereinafter, an original document given an original document ID "Y" is referred to as an "original document Y".

The digitalization time and date are time and date of digitalization of an original document identified by a corresponding original document ID. In a case where the digitalizing device is an image reading device, the digitalization time and date can be called reading time and date.

The digitalizing device ID is identification information for identifying a device used to digitalize an original document identified by a corresponding original document ID. Typically, the digitalizing device is an image reading device that reads an image of an original document to digitalize the original document.

The page configuration is a page number of a page that constitutes a form under confirmation identified by a corresponding form-under-confirmation ID. The page number is a number of the page given in an order of digitalization of pages of an original document by a digitalizing device. In a case where the digitalizing device is an image reading device, the page number can be said a number in an order of reading of pages of an original document by the image reading device.

FIG. 10 shows, for example, that a form under confirmation SN30037-1 including pages of page numbers 1 and 3, a form under confirmation SN30037-2 including pages of page number of 4 to 7, and a form under confirmation SN30037-6 including pages of page numbers of 23 to 26 are managed among sorted forms obtained by sorting forms obtained by digitalizing an original document SN30037 at the same digitalization time and date by the same digitalizing device.

FIG. 11 illustrates an example of stray page information stored in the stray page information storage unit 22.

As illustrated in FIG. 11, the stray page information is information in which a stray page ID, an original document ID, a digitalization time and date, a digitalizing device ID, and a page number are associated with one another.

The stray page ID is identification information for identifying a stray page. Hereinafter, a stray page given a stray page ID "X" is referred to as a "stray page X".

The original document ID, the digitalization time and date, and the digitalizing device ID have been already described in relation to FIG. 10, and repeated description thereof is omitted.

The page number is a number of a page given in an order of digitalization of pages of an original document identified by a corresponding original document ID by a digitalizing device, as described above. In a case where the digitalizing device is an image reading device, the page number can be said a number in an order of reading of pages of an original document by the image reading device.

FIG. 11 shows, for example, that a stray page Lost-SN30037-2 of a page number 2, a stray page Lost-SN30037-8 of a page number 8, a stray page Lost-SN30037-9 of a page number 9, a stray page Lost-SN30037-21 of a page number 21, and a stray page Lost-SN30037-22 of a page number 22 are managed among pages of sorted forms obtained by sorting forms obtained by digitalizing an original document SN30037 at the same digitalization time and date by the same digitalizing device.

FIG. 12 illustrates an example of suspended form information stored in the suspended form information storage unit 23.

As illustrated in FIG. 12, the suspended form information is information in which a suspended form ID, an original document ID, a digitalization time and date, a digitalizing device ID, and a page configuration are associated with one another.

The suspended form ID is identification information for identifying a suspended form. Hereinafter, a suspended form given a suspended form ID "X" is referred to as a "suspended form X".

The original document ID, the digitalization time and date, the digitalizing device ID, and the page configuration have been already described in relation to FIG. 10, and repeated description thereof is omitted.

FIG. 12 shows, for example, that a suspended form Hold-SN30037-3 including pages of page numbers 10 to 13 and a suspended form Hold-SN30037-5 including pages of page numbers 19 and 20 are managed among sorted forms obtained by sorting forms obtained by digitalizing an original document SN30037 at the same digitalization time and date by the same digitalizing device.

Operation of Document Processing Apparatus

In the document processing apparatus 10 according to the present exemplary embodiment, the action receiving unit 25 receives a user's action on the form confirmation screen 30. In response to this, for example, the movement processing unit 26 moves a misplaced page from the form confirmation region 40 to the stray page corner 50 or moves a missing page from the stray page corner 50 to the form confirmation region 40. Furthermore, the movement processing unit 26 moves a form under confirmation in the form confirmation region 40 to the suspended form corner 70 or delivers the form under confirmation to the form output unit 27 to register the form under confirmation as a correct sorted form. First, operation of the movement processing unit 26 is described in detail below.

Figure 13:
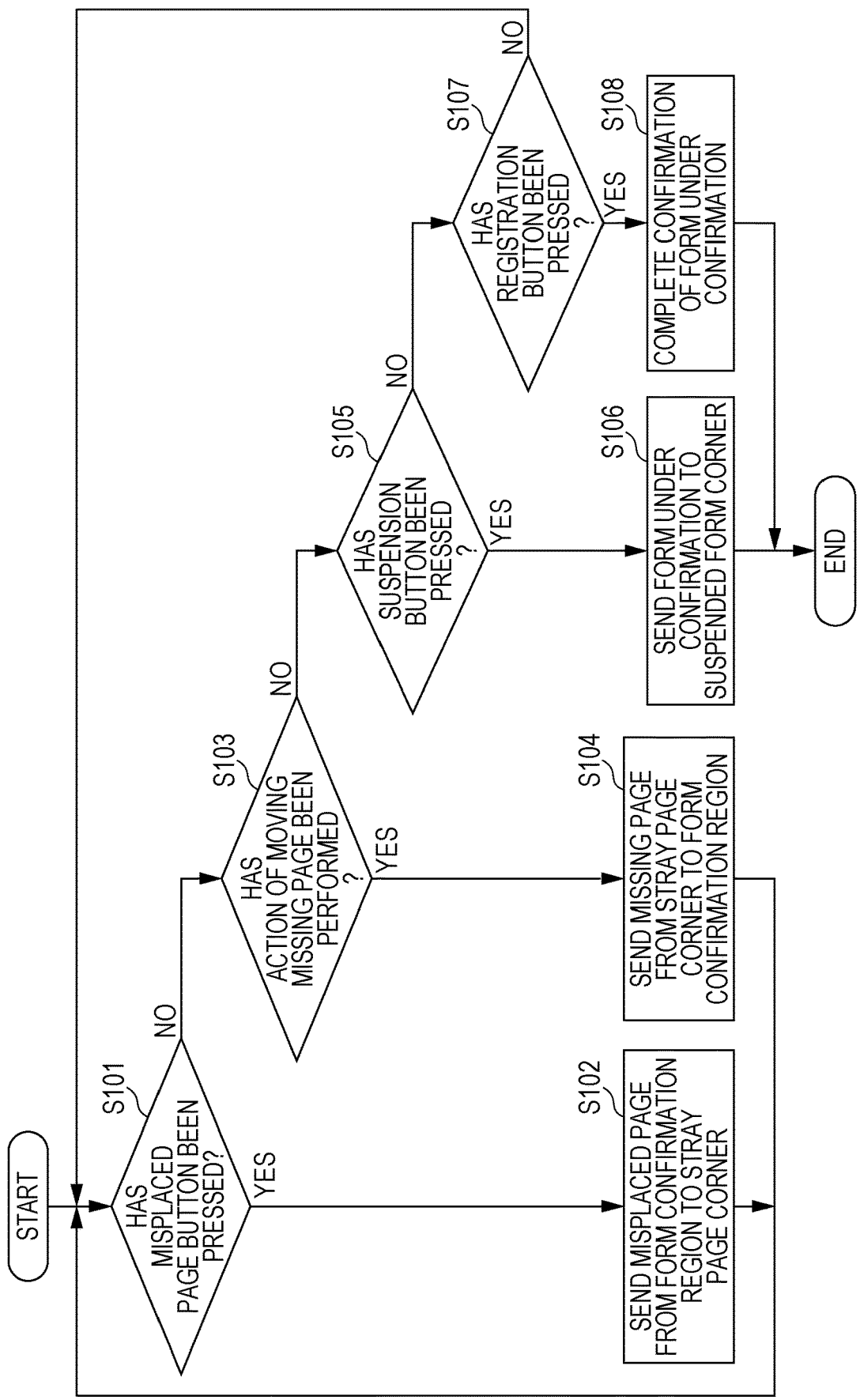
FIG. 13 is a flowchart illustrating an example of operation of a movement processing unit of the document processing apparatus according to the exemplary embodiment of the present disclosure.

FIG. 13 is a flowchart illustrating an example of operation of the movement processing unit 26.

As illustrated in FIG. 13, first, the movement processing unit 26 determines whether or not the action receiving unit 25 has received an action of pressing the misplaced page button 45 on a misplaced page of a form under confirmation displayed in the form confirmation region 40 (step 101).

In a case where it is determined in step 101 that the action receiving unit 25 has received an action of pressing the misplaced page button 45 on the misplaced page of the form under confirmation, the movement processing unit 26 sends the misplaced page of the form under confirmation from the form confirmation region 40 to the stray page corner 50 (step 102). Specifically, the movement processing unit 26 converts a part concerning this misplaced page in a row corresponding to this form under confirmation in the form-under-confirmation information stored in the form-under-confirmation information storage unit 21 into a row corresponding to this misplaced page in the stray page information and adds this row to the stray page information storage unit 22. Then, the processing returns to step 101.

Meanwhile, it is determined in step 101 that the action receiving unit 25 has not received an action of pressing the misplaced page button 45 on the misplaced page of the form under confirmation, the movement processing unit 26 determines whether or not the action receiving unit 25 has received an action of moving a missing page of the form under confirmation from the stray page corner 50 (step 103).

In a case where it is determined in step 103 that the action receiving unit 25 has received an action of moving the missing page of the form under confirmation from the stray page corner 50, the movement processing unit 26 sends the missing page of the form under confirmation from the stray page corner 50 to the form confirmation region 40 (step 104). Specifically, the movement processing unit 26 converts a row corresponding to this missing page in the stray page information stored in the stray page information storage unit 22 into a part concerning a page into which the missing page is to be inserted in a row corresponding to this form under confirmation in the form-under-confirmation information stored in the form-under-confirmation information storage unit 21 and adds this part to the form-under-confirmation information storage unit 21. Then, the processing returns to step 101.

Meanwhile, in a case where it is determined in step 103 that the action receiving unit 25 has not received an action of moving the missing page of the form under confirmation from the stray page corner 50, the movement processing unit 26 determines whether or not the action receiving unit 25 has received an action of pressing the suspension button 43 (step 105).

In a case where it is determined in step 105 that the action receiving unit 25 has received an action of pressing the suspension button 43, the movement processing unit 26 sends a form under confirmation displayed in the form confirmation region 40 to the suspended form corner 70 (step 106). Specifically, the movement processing unit 26 converts a row corresponding to this form under confirmation in the form-under-confirmation information stored in the form-under-confirmation information storage unit 21 into a row corresponding to this form under confirmation in the suspended form information and adds this row to the suspended form information storage unit 23. Then, the processing ends.

Meanwhile, in a case where it is determined in step 105 that the action receiving unit 25 has not received an action of pressing the suspension button 43, the movement processing unit 26 determines whether or not the action receiving unit 25 has received an action of pressing the registration button 44 (step 107).

In a case where it is determined in step 107 that the action receiving unit 25 has not received an action of pressing the registration button 44, the movement processing unit 26 returns the processing to step 101.

Meanwhile, in a case where it is determined in step 107 that the action receiving unit 25 has received an action of pressing the registration button 44, the movement processing unit 26 completes confirmation of the form under confirmation displayed in the form confirmation region 40 (step 108). That is, the movement processing unit 26 delivers the form under confirmation displayed in the form confirmation region 40 to the form output unit 27 to register this form under confirmation as a correct sorted form. Specifically, the movement processing unit 26 deletes a row corresponding to this form under confirmation in the form-under-confirmation information stored in the form-under-confirmation information storage unit 21 and delivers this row to the form output unit 27. Then, the processing ends.

The display control unit 24 controls the display device 15 to display the form confirmation screen 30 or the suspended form screen 60 on the basis of the form-under-confirmation information and the stray page information updated in steps 102 and 104, the form-under-confirmation information and the suspended form information updated in step 106, or the form-under-confirmation information updated in step 108.

In addition, the form output unit 27 outputs the form under confirmation delivered from the movement processing unit 26 to an outside to register this form under confirmation as a correct sorted form.

In the document processing apparatus 10 according to the present exemplary embodiment, in a case where plural users are involved with work of confirming sorted forms in cooperation, a notification is given upon addition of a new stray page to the stray page corner 50 so that a user who is in charge of a suspended form that is likely to be filled by the new stray page is prompted to confirm the new stray page. Next, operation of the notification processing unit 28 in this case is described in detail below.

Figure 14:
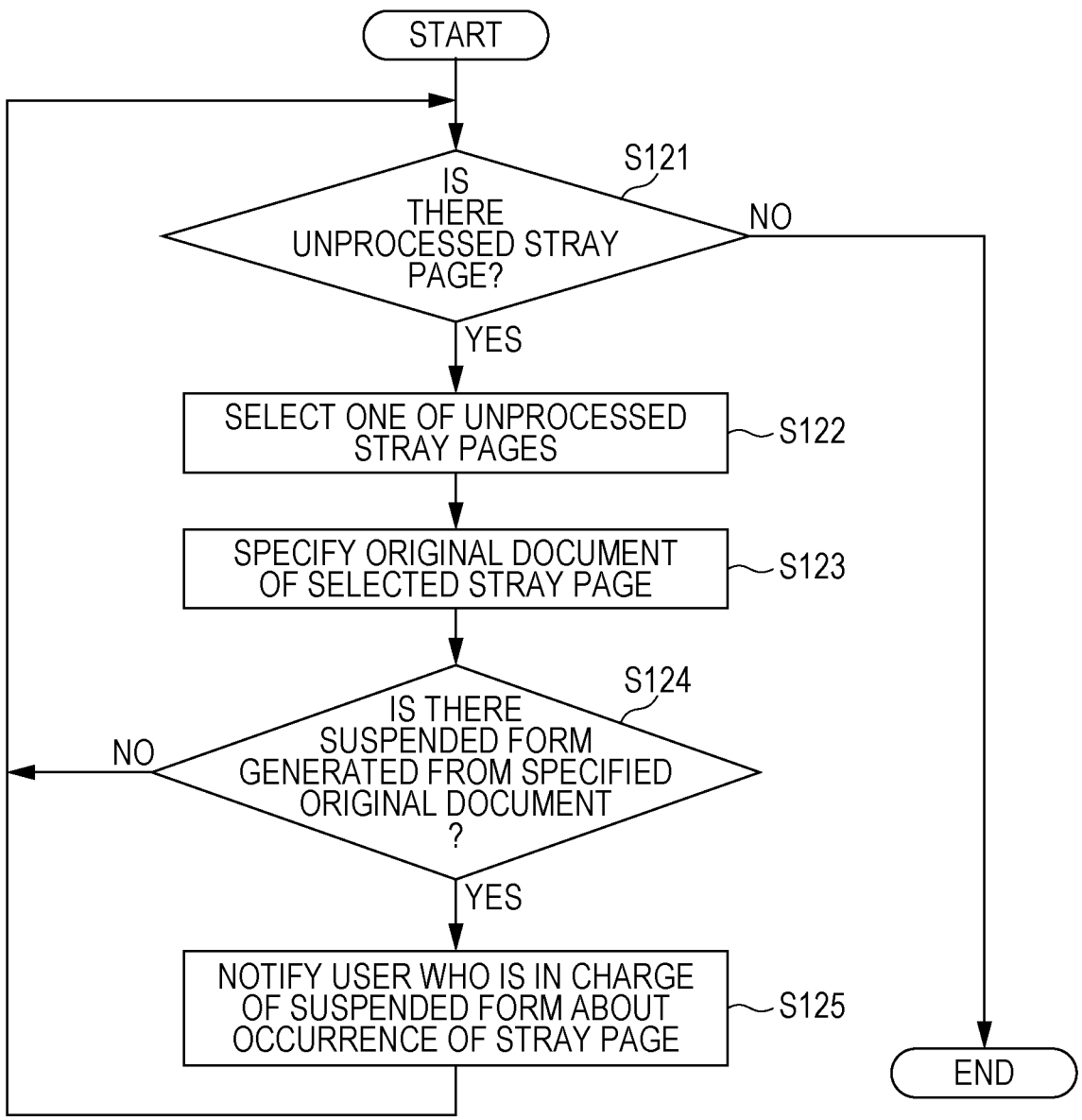
FIG. 14 is a flowchart illustrating an example of operation of a notification processing unit of the document processing apparatus according to the exemplary embodiment of the present disclosure.

FIG. 14 is a flowchart illustrating an example of operation of the notification processing unit 28 in a case where a new stray page is put into the stray page corner 50. Note that the operation in this flowchart is regularly executed.

As illustrated in FIG. 14, first, the notification processing unit 28 determines whether or not there is an unprocessed stray page that has been put after previous operation (step 121).

In a case where it is determined in step 121 that there is(are) an unprocessed stray page(s), the notification processing unit 28 selects one of the unprocessed stray pages (step 122).

The notification processing unit 28 thus specifies an original document of the stray page selected in step 122 (step 123). Specifically, the notification processing unit 28 acquires an original document ID corresponding to the stray page selected in step 122 from the stray page information stored in the stray page information storage unit 22.

Then, the notification processing unit 28 determines whether or not there is a suspended form generated from the original document specified in step 123 (step 124). Specifically, the notification processing unit 28 determines whether or not there is a row including the original document ID acquired in step 123 in the suspended form information stored in the suspended form information storage unit 23.

In a case where it is determined in step 124 that there is a suspended form generated from the original document, the notification processing unit 28 notifies a user who is in charge of the suspended form about occurrence of the stray page (step 125). Then, the processing returns to step 121.

In a case where it is determined in step 124 that there is no suspended form generated from the original document, the notification processing unit 28 returns the processing to step 121 without notifying a user about occurrence of the stray page.

Meanwhile, in a case where it is determined in step 121 that there is no unprocessed stray page, the notification processing unit 28 finishes the processing.

Furthermore, in the document processing apparatus 10 according to the present exemplary embodiment, it is determined that a suspended form put into the suspended form corner 70 has occurred not because erroneous sorting has occurred but because a page of an original document is missing from the start in a case where all sorted forms obtained by sorting forms obtained by digitalizing the original document at the same time and date by the same device have been confirmed and the number of stray pages that has occurred from the original document is 0, and a user who is in charge of the suspended form is given a notification prompting the user to deal with this. Next, operation of the notification processing unit 28 in this case is described in detail below.

FIG. 15 is a flowchart illustrating an example of operation of the notification processing unit 28 concerning a suspended form put into the suspended form corner 70. Note that the operation in this flowchart is regularly executed.

As illustrated in FIG. 15, first, the notification processing unit 28 selects one suspended form (step 141).

The notification processing unit 28 thus specifies an original document of the suspended form selected in step 141 (step 142). Specifically, the notification processing unit 28 acquires an original document ID corresponding to the suspended form selected in step 141 from the suspended form information stored in the suspended form information storage unit 23.

Then, the notification processing unit 28 determines whether or not there is a form under confirmation generated from the original document specified in step 142 (step 143). Specifically, the notification processing unit 28 determines whether or not there is a row including the original document ID acquired in step 142 in the form-under-confirmation information stored in the form-under-confirmation information storage unit 21.

In a case where it is determined in step 143 that there is no form under confirmation generated from the original document, the notification processing unit 28 determines whether or not there is a stray page that has occurred from the original document specified in step 142 (step 144). Specifically, the notification processing unit 28 determines whether or not there is a row including the original document ID acquired in step 142 in the stray page information stored in the stray page information storage unit 22.

In a case where it is determined in step 144 that there is no stray page that has occurred from the original document, the notification processing unit 28 notifies a user who is in charge of the suspended form selected in step 141 about missing of a page of the original document (step 145). Then, the processing ends.

Meanwhile, in a case where it is determined in step 143 that there is a form under confirmation generated from the original document or in a case where it is determined in step 144 that there is a stray page that has occurred from the original document, the notification processing unit 28 ends the processing without notifying the user about missing of a page of the original document.

Processor

In the embodiment above, the term "processor" refers to hardware in a broad sense. Examples of the processor include general processors (e.g., CPU: Central Processing Unit), and dedicated processors (e.g., GPU: Graphics Processing Unit, ASIC: Application Integrated Circuit, FPGA: Field Programmable Gate Array, and programmable logic device).

In the embodiment above, the term "processor" is broad enough to encompass one processor or plural processors in collaboration which are located physically apart from each other but may work cooperatively. The order of operations of the processor is not limited to one described in the embodiment above, and may be changed.

Program

The processing performed by the document processing apparatus 10 according to the present exemplary embodiment is prepared, for example, as a program such as application software.

That is, a program that realizes the present exemplary embodiment is grasped as a program for causing a computer to realize a function of causing a first region in which any of plural sets into which plural kinds of data have been sorted according to kind is displayed and a second region in which data that is unsuitable for the sorted sets is displayed to be displayed on an identical screen, a function of receiving selection of data displayed in the second region, and a function of sorting the received data into any of the sets displayed in the first region.

The program that realizes the present exemplary embodiment can be offered by a communication unit or may be offered in a recording medium such as a CD-ROM.

The foregoing description of the exemplary embodiment of the present disclosure has been provided for the purposes of illustration and description. It is not intended to be exhaustive or to limit the disclosure to the precise forms disclosed. Obviously, many modifications and variations will be apparent to practitioners skilled in the art. The embodiment was chosen and described in order to best explain the principles of the disclosure and its practical applications, thereby enabling others skilled in the art to understand the disclosure for various embodiments and with the various modifications as are suited to the particular use contemplated. It is intended that the scope of the disclosure be defined by the following claims and their equivalents.

What is claimed is:

1. An information processing apparatus comprising
a processor configured to:
receive scanned data to be sorted into a sorted set from an image reading device including a scanner;
automatically sort the received scanned data according to predefined sorting criteria;
after the automatic sorting is completed, concurrently display, on a same screen,
a first region in which the sorted set is displayed, and
a button which, when pressed, displays a second region in which one or more pieces of the scanned data that could not be automatically sorted into the sorted set due to not satisfying the predefined sorting criteria are displayed;
receive selection of data displayed in the second region;
sort the selected data from the second region into the sorted set displayed in the first region; and
register the sorted set displayed in the first region as a correct sorted set and output the correct sorted set to an outside of the information processing apparatus,
wherein the processor is further configured to:
in a case where the sorted set has a missing part, manage the sorted set as a suspended set, the suspended set representing a set of data whose sorting is not completed, and
in response to a determination that the missing part of the sorted set managed as the suspended set is not to be filled by sorting, notify a user who is related to the suspended set, of the determination.

2. The information processing apparatus according to claim 1, wherein the processor is configured to
receive user's selection of data that is erroneously sorted into the sorted set among the data included in the sorted set displayed in the first region; and
move the user-selected data from the first region to the second region.

3. The information processing apparatus according to claim 1, wherein the processor is configured to manage the sorted set as the suspended set in a case where a specific condition concerning the second region is met.

4. The information processing apparatus according to claim 1, wherein the processor is configured to
not manage the sorted set as the suspended set in a case where a specific condition concerning the second region is not met.

5. The information processing apparatus according to claim 3, wherein
the specific condition is a condition that no data is displayed in the second region or a condition that the data displayed in the second region has been confirmed by a user.

6. The information processing apparatus according to claim 4, wherein
the specific condition is a condition that no data is displayed in the second region or a condition that the data displayed in the second region has been confirmed by a user.

7. The information processing apparatus according to claim 1, wherein
data including information similar to information on the sorted set displayed in the first region is preferentially displayed in the second region, the similarity of the information being similarity of at least one of a location in a page order, a layout, a type of an image reading device, a read time and date, and a location of an image reading device.

8. The information processing apparatus according to claim 7, wherein
the data including the information similar to the information on the sorted set displayed in the first region is data read by an image reading device within a predetermined range from an image reading device used to read the sorted set displayed in the first region at time and date within a predetermined range from time and date of the reading of the sorted set displayed in the first region.

9. The information processing apparatus according to claim 1, wherein the processor is configured to
give a notification indicating that new data has been added to the second region to a user when the new data is added to the second region.

10. The information processing apparatus according to claim 9, wherein
the notification indicating that the new data has been added to the second region is preferentially given to a user who is related to a set including information similar to information on the new data added to the second region, such that the user who is related to the set notices the notification earlier than a user who is not related to the set.

11. The information processing apparatus according to claim 10, wherein
the set including the information similar to the information on the new data added to the second region is a set read by an image reading device within a predetermined range from an image reading device used to read the new data added to the second region at time and date within a predetermined range from time and date of the reading of the new data added to the second region.

12. A non-transitory computer readable medium storing a program causing a computer to execute a process for information processing, the process comprising:
receiving scanned data to be sorted into a sorted set from an image reading device including a scanner;
automatically sorting the received scanned data according to predefined sorting criteria;
after the automatic sorting is completed, concurrently displaying, on a same screen,
a first region in which a sorted set is displayed, and
a button which, when pressed, displays a second region in which one or more pieces of the scanned data that could not be automatically sorted into the sorted set due to not satisfying the predefined sorting criteria are displayed;

receiving selection of data displayed in the second region;

sorting the selected data from the second region into the sorted set displayed in the first region; and registering the sorted set displayed in the first region as a correct sorted set and output the correct sorted set to an outside of the information processing apparatus, wherein the process further comprises:

in a case where the sorted set has a missing part, managing the sorted set as a suspended set, the suspended set representing a set of data whose sorting is not completed, and in response to a determination that the missing part of the sorted set managed as the suspended set is not to be filled by sorting, notifying a user who is related to the suspended set, of the determination.

13. An information processing method performed by an information processing apparatus, the method comprising:

receiving scanned data to be sorted into a sorted set from an image reading device including a scanner;

automatically sorting the received scanned data according to predefined sorting criteria;

after the automatic sorting is completed, concurrently displaying, on a same screen, a first region in which a sorted set is displayed, and a button which, when pressed, displays a second region in which one or more pieces of the scanned data that could not be automatically sorted into the sorted set due to not satisfying the predefined sorting criteria are displayed;

receiving selection of data displayed in the second region;

sorting the selected data from the second region into the sorted set displayed in the first region; and registering the sorted set displayed in the first region as a correct sorted set and output the correct sorted set to an outside of the information processing apparatus, wherein the method further comprises:

in a case where the sorted set has a missing part, managing the sorted set as a suspended set, the suspended set representing a set of data whose sorting is not completed, and in response to a determination that the missing part of the sorted set managed as the suspended set is not to be filled by sorting, notifying a user who is related to the suspended set, of the determination.

14. The information processing apparatus according to claim 1, wherein the scanned data to be sorted into a sorted set is received from a plurality of separate scanners.

* * * * *